United States Patent [19]

Shimizu et al.

[11] 4,356,268

[45] Oct. 26, 1982

[54] MICROORGANISM FOR TREATING WASTE WATER

[75] Inventors: Norio Shimizu; Yoji Odawara, both of Hitachi; Yasunori Masaki, Yamaguchi, all of Japan

[73] Assignee: Hitachi, Ltd., Tokyo, Japan

[21] Appl. No.: 213,222

[22] Filed: Dec. 5, 1980

Related U.S. Application Data

[62] Division of Ser. No. 46,236, Jun. 7, 1979, abandoned.

[30] Foreign Application Priority Data

Sep. 22, 1978 [JP] Japan .................................. 53-115813

[51] Int. Cl.³ ............................................ C12N 1/20
[52] U.S. Cl. .................................... 435/253; 435/267; 435/829
[58] Field of Search ............... 210/601, 610, 611, 626, 210/627, 628, 631; 435/62, 253, 829, 267

[56] References Cited

U.S. PATENT DOCUMENTS

| | | | |
|---|---|---|---|
| 3,356,609 | 9/1967 | Bruemmer | 210/627 |
| 3,432,427 | 3/1969 | Moore | 210/601 |
| 3,480,144 | 11/1969 | Barth | 210/626 |
| 3,627,095 | 12/1971 | Srinivason | 435/829 |
| 3,660,278 | 5/1972 | Mimura | 210/611 |
| 3,754,925 | 8/1973 | Kimura | 435/829 |
| 3,756,974 | 9/1973 | Fujii | 210/611 |

OTHER PUBLICATIONS

Kiuchi et al., J. Gen. Appl. Microbiol. 14, 399–409, (1968).
Bergey's Manual of Determinative Bacteriology, 7th Ed., 1959, 296–301.
The Microbiol World, Stanier, 1970, N.J., pp. 639–640.
Hackh's Chemical Dictionary, Grant, Fourth Edition, McGraw-Hill, New York, 1972, 98.

*Primary Examiner*—Ernest G. Therkorn
*Attorney, Agent, or Firm*—Thomas E. Beall, Jr.

[57] ABSTRACT

The invention relates to an improvement of the floc-formation property of activated sludge contained in waste water.

A waste water treatment process comprises steps culturing a novel strain-*Alcaligenes faecalis* HRL-1 - and adding the cultured cells to to-be-treated waste water.

6 Claims, 1 Drawing Figure

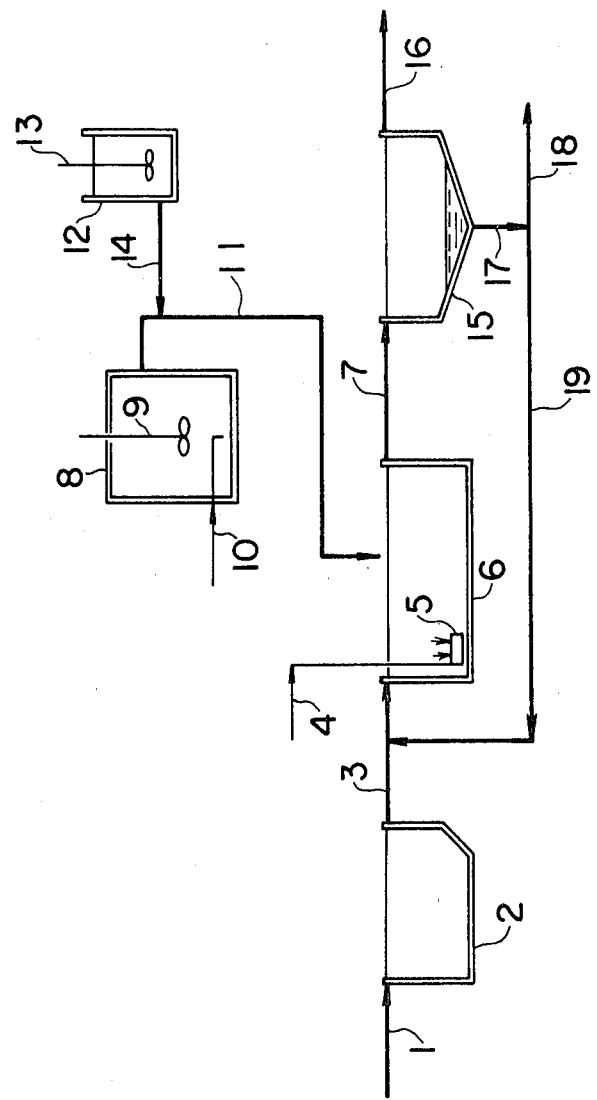

MICROORGANISM FOR TREATING WASTE WATER

This is a division of application Ser. No. 046,236, filed Jun 7, 1979, now abandoned.

This invention relates to a treatment of waste water containing organic materials, namely organic sludge such as city sewage and industrial sewage discharged from various factories.

In order to treat such sludge, a microorganism treatment method which is generally called activated sludge treatment method has been used. According to this treatment method, microorganisms is activated sludge oxidize and decompose organic materials in waste water by using oxygen fed by aeration.

Activated sludge is an assembly of microorganisms including bacteria and protozoa etc.

Concerning activated sludge, *Advances of Applied Microbiology*, pages 77–103 is referred to.

Also, referring to floc formation in activated sludge, *J. Gen. Appl. Microbiol.*, 14, 387 (1968), pages 399–409 describes *Pseudomonas stutzeri* and *Alcaligenes faecalis* as capable to form flocs. Furthermore, *Bergey's Manual of Determinative Bacteriology*, ORDER IV. EUBACTERIALES describes *Alcaligenes faecalis*. One problem involved in the sludge treatment method is that a large area is necessary for a treatment plant. Therefore, various proposals have been made on aeration tanks for solving this problem, but proposals have rarely been made on sedimentation tanks. In addition, degradation of the sedimentation property of activated sludge, called "bulking" is sometimes caused by changes of the quantity and quality of waste water during the activated sludge treatment. When this phenomenon takes place, sedimentation of activated sludge is occurs only sightly and activated sludge is discharged out of the system together with the treated water, resulting in degradation of the quality of treated water and reduction of the concentration of activated sludge returned to the aeration tank. Therefore, sufficient purification of waste water becomes impossible. With the occurrence of this undesirable phenomenon, inorganic coagulating agents such as aluminum sulfate, ferric sulfate aluminum polychloride, or anonic, cationic or nonionic organic polymeric coagulants have heretofore been added. This method, however, is an emergency measure, and the final result is that, activated sludge in the aeration tank should be completely exchanged by normal activated sludge.

SUMMARY OF THE INVENTION

The present invention is to eliminate the foregoing disadvantages involved in the conventional techniques.

An object of the invention is to provide a method for treating waste water in which the sedimentation property of activated sludge is improved by utilizing a novel microorganism to thereby reduce the needed capacity of a sedimentation tank and to decrease the volume of excessive activated sludge.

According to the present invention, this object is attained by a method which comprises culturing strain HRL-1 belonging to *Alcaligenes faecalis*, which is hereinafter called *Alcaligenes faecalis* HRL-1, and adding the culture cells to waste water containing activated sludge.

In addition, according to the present invention, a method is provided, comprising adding the culture cells in an amount equal to 0.1 to 5% of the activated sludge present together with a floc-forming promoting agent such as magnesium ions to form great flocs.

Pursuant to the invention, it is possible to also employ a method which comprises oxidizing and decomposing organic materials in the waste water by blowing air into the waste water containing activated sludge.

*Alcaligenes faecalis* HRL-1 was deposited in the ATCC on May 31, 1979 with deposition number of ATCC No. 31529.

This strain was also deposited at Fermentation Research Institute, Agency of Industrial Science and Technology, in Japan, with deposition number in FERM-P No. 4564 on Aug. 5, 1978.

BRIEF DESCRIPTION OF THE DRAWING

The drawing illustrates a flow-diagram showing a method for treating waste water embodying the present invention.

DESCRIPTION OF THE INVENTION

Isolation of *Alcaligenes faecalis* HRL-1

*Alcaligenes faecalis* HRL-1 is a novel strain belonging to *Alcaligenes faecalis* which was separated by us from activated sludge fed to a wasted water treating facility located in Hitachi-city, Ibaraki-ken, Japan.

Activated sludge was extracted from an activated sludge treatment system which was operated under a high load condition more than 10 kg/m$^3$.d of BOD load by volume. The activated sludge was washed three times with physiological saline of 0.8% concentration and dispersed with a homogenizer. Thereby, a microorganism suspension was produced. The microorganism suspension was diluted with physiological saline, plated out on nutrient agar medium containing a sludge extract (referred to Kiuchi et al., *J. Gen Appl. Microbiol.*, 14, 387(1968)) and cultured for three days at a temperature of 25° C. Then, the cultured microorganisms were isolated and, after that, *Alcaligenus faecalis* HRL-1 was separated from the cultured microorganisms.

Culture of *Alcaligenes faecalis* HRL-1

The separated *Alcaligenes faecalis* HRL-1 was cultured or incubated under the following conditions.

Medium: Saccharides like glucose and sucrose, and accetate.

Source of nitrogen: Peptone, amino acids and ammoniate.

Source of phosphorus: Phosphates like $KH_2PH_4$.

Inorganic salt: $Mg^{++}$, $Ca^{++}$ or $Fe^{++}$.

Vitamin: Biotin

PH: 7

Temperature: 25° to 30° C.

It is possible to culture *Alcaligenes faecalis* HRL-1 by using Nutrient broth which is employed for incubating general bacteria.

Bacteriological characteristics of *Alcaligenes faecalis* HRL-1

*Alcaligenes faecalis* HRL-1 has the following baterological characteristics. The determination of the bacterium was carried out according to *Bergey's Manual of Determinative Bacteriology*, 7th ed. In addition, the incubation was carried out at a temperature of 25° C.

I Morphological characteristics

The form of the baterium incubated on the nutrient agar medium for 24 hours is a straight rod of 0.5 by 1.5

2.0 μm occuring singly. Gram stain is negative. Motile with one or several flagella. No spore formation and no acid fast.

II Cultural Characteristics

1. Nutrient agar colonny: Circular, entire, convex, opaque, smooth, glistening. The inside is homogeneous, the hardness is sticky and tone of color represents light brown.
2. Nutrient agar slant: Growth moderate, filiform, opaque, butterlike. Surface is rough and edge is erose. Tone of color represents light brown.
3. Nutrient broth: Thin pellicle, turbid, sediment. Gives off ammonia.
4. Gelatin stab: No liquefaction at 20° C. Light red surface growth.
5. BCP milk: Alkaline and slightly peptonized.

III Physiological Characteristics

1. Reduction of nitrate to nitrite: Positive.
2. Denitrification: Positive.
3. Methyl red test: Negative.
4. VP test: Negative.
5. Production of indole: Negative.
6. Production of hydrogen sulfide: Negative.
7. Hydrolysis of starch: Negative.
8. Utilization of citric acid: No utilization of Koser medium. Utilization at Christensen medium.
9. Utilization of inorganic nitrogen source: Not utilize nitrate. Utilizes ammoniate.
10. Pigmentation: Negative.
11. Urease: Positive.
12. Oxidase: Positive.
13. Catalase: Positive.
14. Range of growth: Not grow at PH 4.95. Grows at PH 6.05 to 10.1. Optimum at PH 7.0. Grows at 10° C. Not grow at 37° C. Optimum at 25° to 30° C.
15. Oxygen demand: Aerobic.
16. O-F test: No acid from glucose.
17. Production of acid and gas from saccharides: Not produce acid and gas from L-arabinose, D-xylose, D-glucose, D-mannose, D-fructose, D-galactose, maltose, sucrose, lactose, trehalose, D-sorbitol, D-mannitol, inositol, glycerol and starch.
18. Not produce 3-Ketolactose.

IV Others

1. Requires biotin.
2. Forms easily large flocs visible to the unaided eyes.
3. Preferable to add $Mg^{++}$ in order to form great flocs.

Since the present strain is Gram, negative has mobility, peritrichous flagella and does not produce an acid from saccharides, it is considered that the present strain belongs to *Alcaligenes faecalis*. However, in view of *Alcaligenes faecalis* described in *Bergey's Manual of Determinative Bacteriology*, 7th ed., *Alcaligenes faecalis* Castellani and Chalmers, 1919, the present strain is different from *Alcaligenes faecalis* in three aspects: the present strain is slightly peptonized by BCP milk incubation, is positive to urease and does not grow at a temperature of 37° C. Therefore, the present strain was identified as a novel strain belonging to *Alcaligenes faecalis* and was named "*Alcaligenes faecalis* HRL-1".

With regard to *Alcaligenes faecalis* separated from activated sludge which forms floc, the report of KIUCHI et al., *J. Gen. Appl. Microbiol.* 14, 399–409 (1968) describes *Alcaligenes faecalis No. 32*. However, *Alcaligenes faecalis* HRL-1 is different from *Alcaligenes faecalis* No. 32 in that *Alcaligenes faecalis* HRL-1 reduces nitric acid and does not grow at a temperature of 37° C.

*Alcaligenes faecalis* is cultured in the presence of magnesium ions and culture cells are added to activated sludge, whereby the sedimentation property of activated sludge can be remarkably improved. The reasons are considered to be as follows. When culture cells of *Alcaligenes faecalis* HRL-1 added to activated sludge, *Alcaligenes faecalis* HRL-1 rapidly propagates in an aeration tank while taking nutrients. During this propagation, *Alcaligenes faecalis* HRL-1 gathers into its own flocs bacteria inferior in the floc-forming property, whereby larger flocs of activated sludge are formed. Accordingly, activated sludge having low density as well as small floc diameter is converted to activated sludge having large and dense flocs, whereby the sedimentation property is improved. This change can be apparently confirmed by observation under microscope.

In order for the present strain to form good flocs, the presence of $Mg^{++}$ is needed and the shortage of $Mg^{++}$ must be compensated for by addition of $Mg^{++}$.

An amount of $Mg^{++}$ necessary for formation of good flocs depends upon the load and it is generally sufficient in concentration of 0.1 to $10 \times 10^{-3}$ mol. About $10^{-}$ mol/l is recommended to form good flocs. It is possible to use $Ca^{++}$ in stead of $Mg^{++}$, but flocculation is inferior to that of $Mg^{++}$. Otherwise, the concentration of $Ca^{++}$ is similar to that of $Mg^{++}$.

In either case, $Mg^{++}$ and $Ca^{++}$, the PH is adjusted to 6 to 8 and the temperature is adjusted to 10° to 35° C.

Good results are ordinarily obtained when cells of the present strain are added in an amount of 0.1 to 5% by weight based on the amount of activated sludge present in the aeration tank, though the preferred amount of the cells varies to some extent depending on the liquid temperature in the aeration tank and the BOD load. The cells may be added to any of the aeration tank, the adjustment tank, the sedimentation tank and the sludge return pipe. Incidentally, cells of the present strain can be used as seed sludge for a newly built waste water treatment plant. In this case, the culturing time can be remarkably shortened.

A waste water treatment process embodying the invention will be now described in detail by reference to a flow-diagram.

Waste water is fed to a preliminary depositing tank 2 through a waste water conduit 1 and non-soluble solids are removed in the preliminary depositing tank 2. The waste water passed through the tank 2 is fed to an aeration tank 6 through a conduit 3 with a returning activated sludge from a returning activated sludge conduit 19.

Also *Alcaligenes faecalis* HRL-1 incubated in incubating tank 8 is supplied to the aeration tank 6 through a conduit 11 with $Mg^{++}$ sent from a $Mg^{++}$ storage tank 12 through a conduit 14. In the aeration tank 6, the waste water, activated sludge, *Alicaligenes faecalis* HRL-1 and $Mg^{++}$ are supplied a sufficient amount of oxygen by a way of aeration from a dispersing plate 5 connected with an air introducing conduit 4 and are mixed with each other and well-stired, so that the purification of waste water is carried out and flocculation is promoted. Continuously, the mixed liquid is fed to a depositing tank 15 through a conduit 7 and rapidly isolated into a solid part and a liquid part in the tank 15. The treated water is discharged out of the system through a treated water discharging conduit 16. The deposited activated sludge is drawn out from an activated sludge conduit 17 and one part of the activated sludge is discharged out of the system through a surplus activated sludge conduit 18 as surplus activated sludge and other part of them is returned to the aeration tank 6 through the returning activated sludge conduit 19 as returning activated sludge.

A stirring device is installed in the incubating tank 8 for stirring the liquid in the tank 8. At the same time, air is introduced into the tank 8 through an air conduit 10. A stirring device 13 is installed in the $Mg^{++}$ storage tank 12 for stirring the liquid in the tank 13.

The present invention will now be described in detail by reference to the following Examples that by no means limit the scope of the invention.

EXAMPLE 1

A culturing flask having a capacity of 500 ml was charged with 100 ml of a culture medium containing 2 g of glucose, 2 g of peptone, 1 g of potassium phosphate and 0.12 g of magnesium sulfate in 1 l of distilled water and having a pH of 7.2, and the culture medium was inoculated with *Alcaligenes faecalis* HRL-1. Culturing was carried out at 25° C. for 24 hours under shaking to obtain 350 mg/l of star-shaped flocs having a size of 2 to 3 mm.

The so obtained cells were added to an aeration tank in an amount equal to 1.2% by weight of inactivated sludge present in the aeration tank in which waste water having a BOD concentration of 2000 mg/l was continuously treated at a BOD volume load of 8 g/ld and a liquid temperature of 11° C. Three days after the addition, the SVI value of activated sludge was reduced to 50 ml/g, it had been 100 ml/g before the addition. In other words, the sedimentation property was improved 2 times, which indicates that the capacity of the sedimentation tank can be reduced to about ½.

EXAMPLE 2

Cells of *Alcaligenes faecalis* HRL-1 obtained by culturing in the same manner as described in Example 1 were added in an amount of 2.6% by weight to activated sludge having a reduced sedimentation property in an activated sludge treatment plant where waste water having a BOD concentration of 2000 mg/l was continuously treated at a BOD load of 5 g/ld and a liquid temperature of 11° C. Six days after the addition, the SVI value of activated sludge was reduced to 100 ml/g, it had been 200 ml/g before the addition, and the normal sedimentation state was restored. Separation of activated sludge in the sedimentation tank was performed under good conditions, and the quality of treated water was improved.

EXAMPLE 3

A culturing flask having a capacity of 500 ml was charged with 100 ml of a bouillon culture medium, and the culture medium was inoculated with *Alcaligenes faecalis* HRL-1. Culturing was conducted at 25° C. for 24 hours under shaking. The resulting culture cells and $Mg^{++}$ were added in amounts of 0.1% by weight and $10^{-3}$ mole/l to activated sludge present in an aeration tank where waste water having a BOD concentration of 5000 mg/l was continuously treated at a BOD volume load of 20 g/ld and a liquid temperature of 25° C. When two days had passed from the addition, the SVI value of activated sludge was reduced to 70 ml/g, it had been 250 ml/g before the addition. Thus, the sedimentation property was improved about 4 times. Separation of activated sludge in the sedimentation tank was performed under good conditions, and the quality of treated water was highly improved.

As will be apparent from the foregoing illustration, according to the present invention, by adding culture cells of *Alcaligenes faecalis* HRL-1 to activated sludge in an actually operated activated sludge treatment plant, the sedimentation property of activated sludge can be improved, and hence, the volume of the sedimentation tank can be reduced.

What is claimed is:

1. A biologically pure culture of the microorganism *Alcaligenes faecalis* having the identifying characteristics of ATCC 31529, said culture being:
   capable of growth at 10° C.;
   incapable of growth at 37° C.;
   capable of reducing nitrate to nitrite;
   incapable of utilizing nitrate as source of inorganic nitrogen;
   incapable of growth at pH 4.95;
   capable of hydrolyzing urea; and
   capable of forming flocs when mixed with activated sludge in a waste water treatment process.

2. The biologically pure culture of claim 1, which requires biotin for growth.

3. The biologically pure culture of claim 1, wherein the *Alcaligenes faecalis* is cultured in the presence of magnesium ions.

4. The biologically pure culture of either of claims 1 or 2, which is capable of forming flocs.

5. The biologically pure culture of either of claims 1 or 3, which is capable of forming flocs when mixed with activated sludge in a waste water treatment process.

6. A biologically pure culture of *Alcaligenes faecalis* HRL-1 (ATCC No. 31529).

* * * * *